March 3, 1953 C. M. FULKERTH Plant Pat. 1,172
PEACH TREE
Filed Dec. 5, 1950
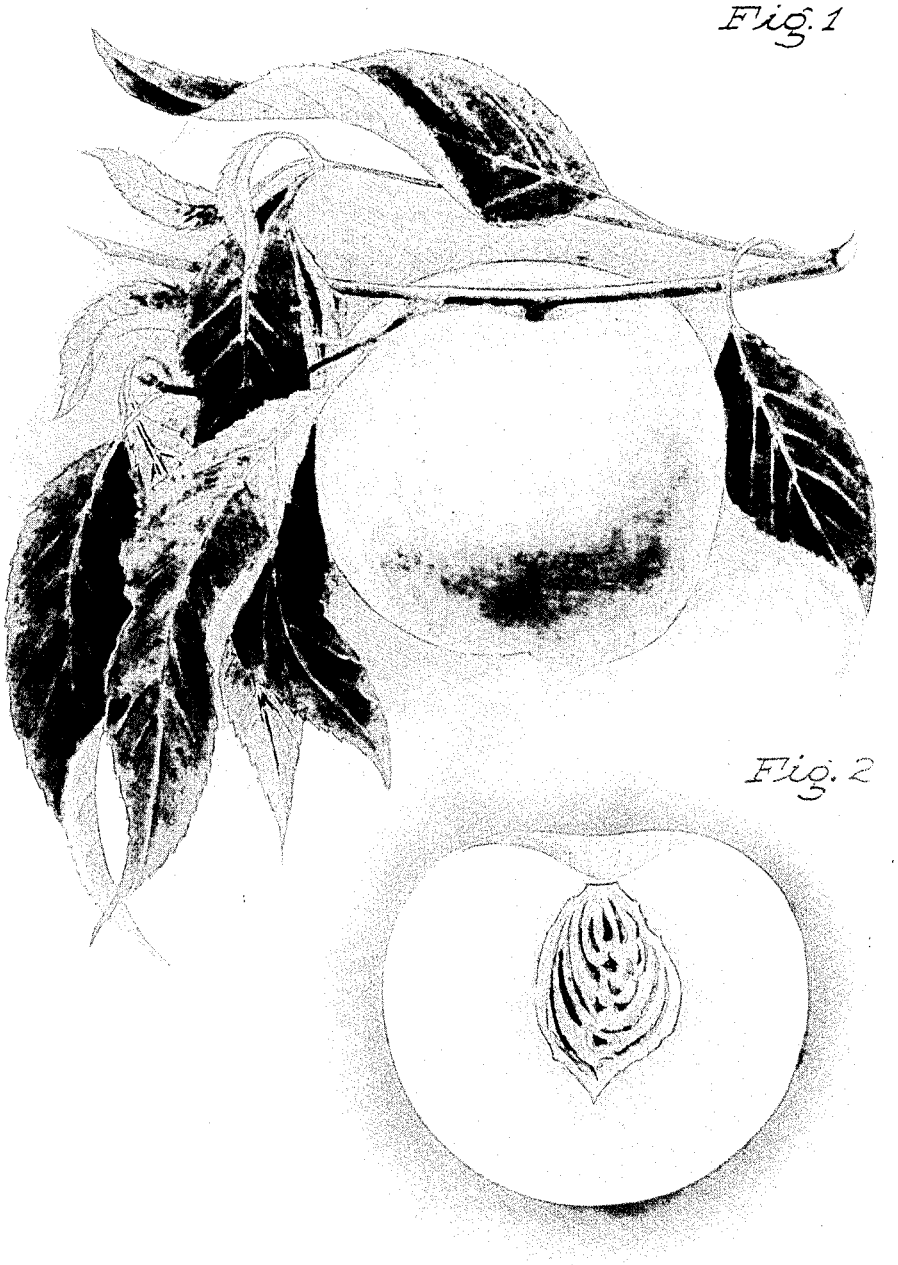
WITNESS
Addison E. Avery
INVENTOR
Carroll M. Fulkerth
Webster & Webster
ATTYS Patented Mar. 3, 1953

Plant Pat. 1,172

UNITED STATES PATENT OFFICE 1,172

PEACH TREE

Carroll M. Fulkerth, Modesto, Calif., assignor of one-half to Willette B. Murray, Modesto, Calif.

Application December 5, 1950, Serial No. 199,254

1 Claim. (Cl. 47—62)

The present discovery relates to a new and distinct variety of peach tree which is vigorous in growth and bears large, yellow-fleshed freestone fruit. This variety is generally of the Elberta type, and while its exact ontogeny is not known, the variety originated in the following manner:

Being a horticulturist by training and engaging in the avocation of growing certain fruit and nut trees with the aim of obtaining superior varieties, I planted a number of Elberta peach seeds along a fence in the garden at my residence in Modesto, California, and a number of open-pollinated seedlings resulted. These seedlings were carefully observed by me, with the result that the instant variety was recognized as being distinct, and was then selected by me for propagation; the variety being of stronger growth and bearing fruit which was distinctive in its characteristics.

In addition to bearing large, yellow-fleshed freestone fruit of an attractive color (red blushed and mottled over in its substantial entirety), the major advantage is that the fruit ripens, and is thus available to the market, approximately two weeks earlier than the Fay Elberta; i. e. the first picking—in the area where grown in California—being on or about July 24th, extending to or about August 13th.

The fruit of this new variety has fine shipping quality, being resistant to deterioration in transit.

The variety has been reproduced by budding onto root stock at the College of Agriculture, University of California, at Davis, California—and additionally—by budding onto a substantial number of Rio Oso Gem peach root stock on the ranch of Charles H. Jackson near Escalon, California.

In the drawings:

Fig. 1 is a perspective view of a twig with leaves in connection with a fruit of the variety.

Fig. 2 is a sectional view of the fruit, with the stone exposed.

Referring now in detail to the new and distinct variety of peach tree and its fruit, the same, including asexual reproductions, is characterized by the following specific description, in outline; identification of the major colors being by reference to Maerz and Paul Dictionary of Color:

Tree: Large size; vigorous; upright; spreading; dense; round topped; very productive regular bearer.

Trunk: Medium size; medium texture.

Branches: Medium size; medium texture. Color—brown-grey, dull.

*Lenticels.*—Numerous; large to medium size.

Leaves: Medium size, averaging 6″ in length and 1½″ in width. Lanceolate; acutely pointed; thin; smooth. Color—dark green (23–L–1) on top of leaves, and lighter green (22–K–2) on the under side.

*Leaf twigs.*—Color—light brown (15–J–11).

*Margin.*—Crenate.

*Petiole.*—Short; thick.

*Glands.*—Average number—three (two or four, rarely six). Opposite; medium size; reniform. Color — green. Position — if two, on upper petiole; if four, two on upper petiole and two on base of blade; and if six, four on petiole and two on base of blade.

*Stipules.*—Dehiscent.

Flower buds: Medium size; medium length; obtuse; appressed to free; pubescent.

Flowers: Medium size. Dates of first and full bloom—February 15th–March 10th, respectively. Blooming period—medium compared with other varieties; color—pink.

Fruit: Maturity when described—ripe.

*Size.*—Uniform; medium. Average diameter axially, 2⅞″; average dimension transversely in suture plane, 2⅞″ to 3″.

*Form.* — Uniform; symmetrical; broadly ovoid.

*Suture.*—Very shallow; extends from base to, but discontinuous at, apex; has slight depression beyond pistil point.

*Ventral surface.*—Sometimes very slightly rounded; lipped toward apex. Lips—equal.

*Cavity.*—Flaring; nearly circular; slightly elongated in suture plane, with suture showing on one side. Average depth, $\frac{9}{16}$″; average breadth, ¼″. Markings—none.

*Base.*—Rounded to truncate; slightly oblique toward the ventral edge.

*Apex.*—Rounded.

*Pistil point.*—Oblique.

Skin: Medium; tender; tenacious to flesh; no tendency to crack. Color—a substantially overall reddish blush and mottling, shading from lighter to darker red (9–H–9 to 3–J–11 to 6–L–6), with a pronounced greyish bloom adjacent the cavity. Down—moderate, medium length.

Flesh: Color—yellow, shading from lighter (9–L–6) to slightly darker (9–L–7), streaked red (3–J–4) next to stone. Surface of pit cavity—red with whitish fibers. Amygdalin—moderate. Juice—moderate, rich. Texture—fine, firm, melting. Fibers—few, tender. Ripens — evenly. Flavor — subacid, mild. Aroma—distinct. Eating quality—good to best.

Stone: Free; parts from flesh smoothly. Size—large to medium, average length 1⅝", average breadth 1⅛", average thickness ¾". Form—oval, full, cuneate toward apex, slightly oblique toward ventral edge. Hilum—oval. Apex—rounded with acuminate tip. Sides—curved on right side. Surface—regularly furrowed near ventral edge—toward apex. Ridges — jagged towards apex. Pits—elongated. Ventral edge—thin. Dorsal edge—narrow, with shallow groove throughout. Ridges—interrupted. Color—brown (14–J–9). Tendency to split—slight.

Use: Market, dessert, canning.

Keeping quality: Good.

The tree and its fruit herein described may vary in slight detail due to climatic and soil conditions under which the variety may be grown.

Having thus described my invention, I claim:

A new and distinct Elberta-type variety of peach tree, substantially as described and illustrated, bearing large yellow-fleshed freestone fruit, characterized by vigorous tree growth; a ripening period of the fruit approximately two weeks earlier than the Fay Elberta; a red blush and mottling over the fruit in its substantial entirety; and fruit of fine shipping quality resistant to deterioration in transit.

CARROLL M. FULKERTH.

No references cited.